(12) United States Patent
Langer et al.

(10) Patent No.: US 10,582,959 B2
(45) Date of Patent: Mar. 10, 2020

(54) SCREW WITH INSERTION POST

(71) Applicant: MEDARTIS HOLDING AG, Basel (CH)

(72) Inventors: Barry Langer, Therwil (CH); Peter Scheuble, Schliengen (DE); Marc Ammann, Pfeffingen (CH); Herbert Polzhofer, Basel (CH)

(73) Assignee: MEDARTIS HOLDING AG, Basel (CH)

( * ) Notice: Subject to any disclaimer, the term of this patent is extended or adjusted under 35 U.S.C. 154(b) by 258 days.

(21) Appl. No.: 15/329,385

(22) PCT Filed: Aug. 3, 2015

(86) PCT No.: PCT/EP2015/067837
§ 371 (c)(1),
(2) Date: Jan. 26, 2017

(87) PCT Pub. No.: WO2016/020329
PCT Pub. Date: Feb. 11, 2016

(65) Prior Publication Data
US 2017/0325862 A1 Nov. 16, 2017

(30) Foreign Application Priority Data
Aug. 5, 2014 (DE) .................... 20 2014 006 372 U

(51) Int. Cl.
*A61B 17/86* (2006.01)
*A61B 17/88* (2006.01)
*A61B 90/00* (2016.01)

(52) U.S. Cl.
CPC ...... *A61B 17/8605* (2013.01); *A61B 17/8872* (2013.01); *A61B 17/8615* (2013.01); *A61B 2090/037* (2016.02)

(58) Field of Classification Search
CPC .............................. A61B 17/86; A61B 17/8685
See application file for complete search history.

(56) References Cited

U.S. PATENT DOCUMENTS 5,971,987 A * 10/1999 Huxel ................ A61B 17/8605
411/2
6,723,099 B1 * 4/2004 Goshert ............ A61B 17/0642
606/329

(Continued)

FOREIGN PATENT DOCUMENTS

AT          513515 A4     5/2014
DE       43 23 434 C1    2/1995

(Continued)

OTHER PUBLICATIONS

German Search Report Corresponding to 20 2014 006 372.9 dated Mar. 3, 2015.

(Continued)

*Primary Examiner* — Nicholas W Woodall
(74) *Attorney, Agent, or Firm* — Davis & Bujold PLLC; Michael J. Bujold

(57) ABSTRACT

A screw (1), in particular a bone screw, comprising a head (16), a shaft (2) and a point (15). The screw (1) has a recess (4) with a contour (5) on a head side (3), The screw (1) is provided with an insertion post (8) in the recess (4), which insertion post is connected to the screw (1) via a predetermined breaking point (7). After breaking the predetermined breaking point and separation of the insertion post (6) from the screw (12), a counter-contour (13) of a tool (12) can be brought into operative connection with the contour (5) of the recess (4). The predetermined breaking point (7) is arranged within the recess (4) such that, after removal of the insertion post (6), a transmission of torque is possible between the tool (12) and the screw (1) via the contour (5) and the counter-contour (13).

21 Claims, 7 Drawing Sheets

(56) References Cited

U.S. PATENT DOCUMENTS

Figure 1A:
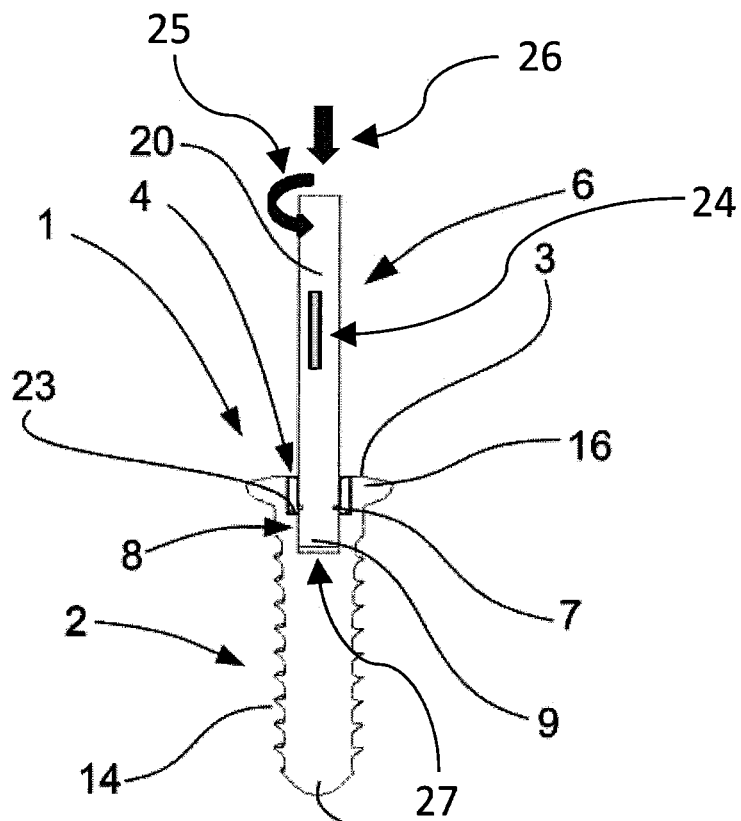

| | | | | |
|---|---|---|---|---|
| 6,964,665 | B2* | 11/2005 | Thomas | A61B 17/7041 606/279 |
| 7,846,167 | B2* | 12/2010 | Garcia | A61B 17/862 606/104 |
| 8,556,938 | B2* | 10/2013 | Jackson | A61B 17/7008 606/269 |
| 2003/0125749 | A1* | 7/2003 | Yuan | A61B 17/1655 606/104 |
| 2007/0218750 | A1 | 9/2007 | Corrao et al. | |
| 2007/0270859 | A1* | 11/2007 | Companioni | A61B 17/8605 606/279 |
| 2012/0150237 | A1 | 6/2012 | Combrowski | |
| 2012/0239052 | A1* | 9/2012 | Beger | A61B 17/8685 606/96 |
| 2015/0196340 | A1 | 7/2015 | Combrowski | |

FOREIGN PATENT DOCUMENTS

| | | |
|---|---|---|
| DE | 10 2009 003 177 A1 | 11/2010 |
| DE | 10 2010 016 812 A1 | 3/2011 |
| DE | 10 2012 104 973 A1 | 3/2013 |
| FR | 2 768 781 A1 | 3/1999 |
| FR | 2 781 998 A1 | 2/2000 |
| FR | 2 983 396 A1 | 6/2013 |
| WO | 97/27812 A1 | 8/1997 |

OTHER PUBLICATIONS

International Search Report Corresponding to PCT/EP2015/067837 dated Oct. 28, 2015.
Written Opinion Corresponding to PCT/EP2015/067837 dated Oct. 28, 2015.

* cited by examiner

SCREW WITH INSERTION POST

The invention relates to screws having an insertion post, and to methods for producing screws having an insertion post as per the preamble of the independent claims.

Below, for simplicity, the invention will be described on the basis of bone screws. This is however in no way to be understood as being restrictive. The screws according to the invention may also be used in other fields in which screws are required.

Screws are used where it is sought to fix individual parts to one another. For example, bone parts are fixed by way of bone screws after a fracture. Here, use is often also made of bone plates which are fixed to the bone by way of screws.

During the screwing-in of screws, there is the risk of the screw being screwed in so tightly that parts of the screw or of the bone are damaged. This can result in the function of the screw no longer being ensured. Furthermore, the drive can be damaged, whereby a removal of the screw by unscrewing can no longer be ensured. This may occur specifically in the case of tightening being performed by machine, in the case of which the increase of torque is less noticeable, or not noticeable, to the user.

WO 97/27812 proposes the provision of a bone screw which, is present in the form of a unit with a screwing-in tool. The screwing-in tool has a shank which is connected to a so row head. A predetermined breaking point is formed in the attachment region between the head and the shank. Said unit is screwed into the bone. During the screwing-in, the torque acting on the predetermined breaking point increases. When the screwing-in depth has been reached, the torque is so great that the screw body breaks off from the shank at the predetermined breaking point.

A part of the screwing-in tool remains connected to the screw head. Here, the breaking point may be rough and may irritate or damage surrounding tissue. Furthermore, the break contour prevents a conventional unscrewing tool from being able to be inserted into the screw head when it is sought to release the screw again. To remove the screw, a special tool is therefore required. Such special tools are firstly very expensive, and secondly, they are not always available to physicians specializing in explanations.

It is therefore the object of the present invention to provide a screw which avoids the disadvantages of the known prior art. In particular, it is the object of the present invention to provide a screw in the case of which the breaking point cannot damage the surrounding tissue and which can be easily released again.

According to the invention, the problem is solved as per the features of the independent claims. Here, a screw, in particular a bone screw, having a head, having a shank and having a tip is proposed. The screw, on the head side, has a recess with a contour. A mating contour of a tool can be placed in operative connection with the contour of the recess. The screw is furthermore equipped, in the recess, with an insertion post. Here, the insertion post is connected to the bone screw by way of a predetermined breaking point. The predetermined breaking point is arranged within the recess such that, after the breaking avid removal of the insertion post, a transmission of torque between the tool, and the screw is possible by way of the contour and mating contour.

The screw tip generally describes the end situated opposite the head side of the screw. Here, the screw tip need not imperatively be of pointed form, but rather may also be of rounded or flattened form, for example.

The head of the screw generally describes an end piece of the screw which has the recess. Here, the screw head need not imperatively be of widened cross section in relation to the shank. The shank and the head may also have the same or even a relatively small cross section.

Here, the shank of the screw is at least partially equipped with a thread. A pitch of the thread may be selected in accordance with the function of the screw. It is also possible for the screw to have a thread with multiple pitches. The thread preferably runs as far as the tip. The thread may be of self-tapping or non-self-tapping form.

The contour of the recess is designed so as to permit a transmission of torque with the mating contour of the tool. It is preferably the case here that the contour is in the form of an internal contour and the mating contour is in the form of an external contour.

It is alternatively conceivable for the contour to be in the form of an external contour. Here, the contour is for example in the form of a pin in the recess. In this embodiment, the mating contour may be in the form of an internal contour which is mounted over the pin.

Within the recess, the screw is connected by way of a predetermined breaking point to an insertion post. The connection is in this case formed directly or indirectly by way of the predetermined breaking point.

A direct connection is to be understood to mean that the predetermined breaking point constitutes the only connecting piece between insertion post and screw.

An indirect connection is to be understood to mean that the connection is realized only by way of at least one further part, preferably a post tip.

In the present case, a post tip is to be understood to mean an end piece of the insertion post, which end piece can be separated from the rest of the insertion pose as a result of breaking of the predetermined breaking point.

The proposed screw can be screwed in by way of the insertion post. During the screwing-in, the torque increases. When a certain torque is reached, the insertion post breaks at the predetermined breaking point. As a result, at least a part of the insertion post which points from the predetermined breaking point in the direction of the head side is released from the screw.

The breaking of the predetermined breaking point preferably occurs before the end position of the screw is reached. By way of the contour of the recess, the screw can subsequently be screwed into the end position by way of the tool.

Alternatively, the unit comprising insertion post and screw is designed such that the predetermined breaking point breaks as soon as the screw has assumed its end position.

Here, the predetermined breaking point prevents an excessively high torque from being generated. By virtue of the fact that the torque cannot become too high, damage to the bone and/or to the screw (e.g. the contour of the screw) or to any plate that is fastened to the screw is prevented. In this way, it is ensured that the screw can perform its fixing function. Furthermore, with an undamaged contour, it is ensured that the screw is easily releasable again when the fixing is no longer required.

Alternatively, the predetermined breaking point may be broken by way of a breaking-off action (bending moment) rather than a turning-off action (torsion moment). This is preferably performed before an end position of the screw is reached. The end position may thereafter in turn be reached by way of the contour of the recess and the mating contour of the tool.

As described above, the tool may serve for bringing the screw into the end position. The tool however also serves for releasing the screw again, for example when the fixing is no longer required. A transmission of torque between the mating contour of the tool and the contour of the recess is necessary for this purpose. The predetermined breaking point between screw and insertion post is arranged so as to be set back within the recess such that, after the breaking at the predetermined breaking point and a removal of the broken-off end of the insertion post, a transmission of torque between the contour of the recess and the mating contour of the tool is possible.

The predetermined breaking point is therefore arranged so as to be set back relative to the head side of the screw; in particular, the predetermined breaking point is arranged so as to be set back by more than 50% of a length of the recess; it is particularly preferable for the predetermined breaking point to be arranged approximately at a level of a base surface of the recess, preferably exactly at the level of the base surface of the recess. The predetermined breaking point is in this case arranged within the screw. In this way, surrounding tissue is not irritated by the breaking point after the breaking of the predetermined breaking point, whereby irritation of and/or damage to the tissue is prevented. Furthermore, the contour is accessible to the tool.

The predetermined breaking point is preferably arranged on that side of the contour which is assigned to the screw tip. Such an arrangement has the result that, after the breaking of the predetermined breaking point and removal of the insertion post, the entire contour is not covered by the predetermined breaking point and/or the possible post tip. In this way, the entire contour is also freely accessible to the mating contour of the tool. This permits a good transmission of torque between tool and screw. Furthermore, in the case of an arrangement of said type, the predetermined breaking point is separated from the head side of the screw at least over the entire length of the contour. The predetermined breaking point is thus not in contact at all with the surrounding tissue.

The recess preferably has, adjoining the contour in the direction of the screw tip, an opening for mounting of the insertion post. Screws having an opening of said type are preferably used in conjunction with insertion posts which are connected indirectly by way of the predetermined breaking point. Here, the post tip can be mounted in the opening. The opening is preferably formed with a smaller diameter than the recess with, the contour. The opening preferably has a contour which differs from the contour of the recess. Here, the predetermined breaking point is preferably arranged at the transition between the opening for the mounting of the insertion post and the contour, that is to say approximately at the level of the base surface of the recess.

The predetermined breaking point may also be arranged within the opening, that is to say below the level of the base surface of the recess.

Alternatively, the predetermined breaking point is formed at the lower end of the recess with contour. In this way, the contour remains largely uncovered, and a transmission of torque between tool and screw remains easily possible.

In the context of the present invention, cannulated screws are also conceivable. Here, a passage hole is formed in the screw. Cannulated screws are conceivable for screws both with or without an opening for the mounting of the insertion post. The passage opening preferably has a smaller diameter than the recess and the opening for the mounting of the insertion post. Alternatively, the opening for mounting is part of the passage opening. Owing to the cannulation, the screw can for example be introduced over a wire (e.g. K-wire) previously placed in the bone.

The predetermined breaking point is preferably in the form of a material weakening with reduced torsion-failure moment and bending-failure moment, preferably in the form of a constriction. The predetermined breaking point is thereby formed so as to be weaker than the insertion post, at least at a section which points in the direction of the head side and which bears against the predetermined breaking point. The predetermined breaking point is preferably weaker than the entirety of the rest of the insertion post. By way of dimensions and/or shape and/or material of the predetermined breaking point, it is possible to define the torque at which the predetermined breaking point breaks.

The predetermined breaking point is preferably formed from the same material, preferably titanium, titanium alloy, implant steel, absorbable metallic or non-metallic material, as the surrounding parts of the insertion post.

The predetermined breaking point may for example be formed by way of a chip-removing process.

Alternatively, the predetermined breaking point may also be formed from some other material. For example, it is conceivable for the insertion post to be manufactured substantially, aside from the predetermined breaking point, from metal, but for the predetermined breaking point to be composed of plastic, an adhesive, some other metal or some other material which exhibits a reduced torsion-failure moment and/or bending-failure moment. The predetermined breaking point may in this case also be formed without a constriction.

The insertion post is preferably equipped with a post tip in integral fashion by way of the predetermined breaking point. Here, the post tip may preferably be mounted in the opening for the mounting of the insertion post.

"Of integral form" means that the insertion post with the predetermined breaking point and post tip is manufactured from, one piece. The post tip can be mounted in the recess, preferably in the opening, such that a torque for the screwing-in of the screw can be transmitted via the post, tip to the screw. Here, the post tip preferably has a post tip contour for the transmission of torque to a post tip mating contour. The post tip preferably remains in the screw after the breaking.

An integral form is easy to produce, because no parts need to be joined together. The post tip contour and the predetermined breaking point are preferably formed into the insertion post.

In an alternative embodiment, the insertion post is formed separately from the post tip. The insertion post is connectable to the post tip by way of the predetermined breaking point. The post tip preferably has a post tip contour for a transmission of torque via a post tip mating contour in the recess, preferably in the opening adjoining the contour of the recess.

In this embodiment, the post tip is connected to the insertion post. The post tip may for example be welded, adhesively bonded, screwed or pressed in. The predetermined breaking point may in this case preferably be formed by virtue of the connecting point between insertion post and post tip exhibiting a reduced torsion-failure moment and/or bending-failure moment in relation to the post tip and the rest of the insertion post.

The predetermined breaking point is preferably configured so as to break in the presence of a twisting-off torque which is less than or equal to the normal tightening torque of said screw.

Typically, in medical applications, said twisting-off torque is not reached during the screwing-in of the shank of the screw. It is normally reached as soon as the screw has reached its end position, that is to say generally when a head or an end piece of the screw strikes a bone plate or the bone. At this moment, the bone and/or the screw have not yet been damaged. The predetermined breaking point is therefore configured such that, firstly, an end position of the screw is reached as a result of screwing-in by way of the insertion post, bat secondly, no damage is caused to the bone and/or to the screw.

Alternatively, higher or deeper torques are conceivable depending on the application.

In a preferred embodiment, the screw and the insertion post are of integral form. The screw and the insertion post are in this case produced from one piece. Here, the predetermined breaking point preferably forms a transition from the screw to the insertion post.

In an alternative embodiment, the insertion post is pressed by way of the post tip into the opening for the mounting of the insertion post.

Here, the insertion post is preferably pressed with an integral post tip into the opening. By way of the post tip, a transmission of torque from the insertion post to the screw is possible.

By way of the pressing-in action, a stable connection can be produced which requires no additional connecting elements.

In a further alternative preferred embodiment, the insertion post is screwed into the opening. Here, the post tip is at least partially equipped with a thread which can be screwed into a mating thread of the opening. In this way, after the screwing-in, the post tip is arranged in the opening. In the case of a cannulated screw, said opening may however be in the form of a passage hole with at least a partial thread.

A screw connection constitutes a stable, releasable connection which requires no additional connecting elements. The predetermined breaking point is preferably formed so as to directly adjoin the thread of the post tip. The tightening torque for the threaded connection is in this case selected to be higher than the screwing-in or unscrewing torque for the screw shank but lower than the twisting-off torque of the predetermined breaking point. Thus, a release of the screw without destruction of the predetermined breaking point is possible during the implantation, for example if it is identified that the screw is not yet seated at the optimum location. Depending on requirements and the field of use, it is possible, for an increase of the tightening torque, to use a connection type additional to the screw connection, preferably a pressed connection. Here, the screwed-in insertion post is preferably additionally pressed in from the outside.

Alternatively, other connections would also be possible, such as for example welding, adhesive bonding, crimping or shrink-fitting of the insertion post into the opening. Depending on the connection type, the connecting point may in this case constitute the predetermined breaking point.

It is also possible for a combination of the above-described connection possibilities to be used.

The contour of the recess is preferably in the form of a slot, cross slot, polygonal socket, multilobular socket or Phillips, particularly preferably in the form of a hexagon or hexalobular ("Torx") socket, that is to say in the form of a standardized contour. Both a hexagon or hexalobular socket form reliable means for torque transmission.

With these preferred contours, no special tool is required in order to release the screw again or tighten the screw further after the breaking of the predetermined breaking point. Since special tools are normally expensive to produce and purchase, a solution with contours such as a hexagon, or hexalobular socket is less expensive. Furthermore, special tools are not always available, and the tightening, and in particular also the unscrewing during the explanation at a clinic/practice which does not have the corresponding tools, would not be possible, or would be possible only with difficulty, in this case.

The insertion post preferably additionally has an insertion contour for transmitting the torque of a commercially available (medical) drilling machine.

The insertion contour may also be in the form of a handle, such as are known for example from screwdrivers.

Alternatively, no special additional contour is formed, and the transmission of torque to the insertion, post is realized without an additional contour, for example in purely fractionally engaging fashion by way of the jaw chuck of a drilling machine.

The various parts of the insertion post and of the screw are preferably composed of titanium, titanium alloy, implant steel, absorbable metallic or non-metallic material.

In particular, the post tip may be composed of absorbable material. The post tip preferably remains in the screw after the breaking of the predetermined breaking point. If the screw is used as a bone screw, the post tip therefore remains in the body, if the post tip still partially covers the contour of the recess, the entire contour is exposed again, as a result of the absorption. This has the effect that the tool with the mating contour can be placed more effectively in operative connection with the contour for the removal of the screw during the explanation. A release of the screw is thereby facilitated.

The insertion post preferably comprises a product-specific labelling, preferably a batch number, a barcode or a logo. The product-specific labelling can be read off and/or preserved after the breaking of the predetermined breaking point.

By way of the labelling, the implanted screw can, with the knowledge of the severed-off insertion post, be subsequently identified.

A further aspect of the invention relates to a set having at least one screw according to the invention and having a tool which has a mating contour, which is complementary to the contour of the recess, of the screw.

A further aspect of the invention relates to a set having at least one bone plate and having at least one screw according to the invention as described above.

Here, the screw(s) preferably serve(s) for the fixing of the bone plate(s) to the bone. The screw(s) and the bone plate(s) may in this case have a blocking contour or a thread, whereby the screw can be blocked in the plate. Details of the blocking are described e.g. in EP 1 608 278 A1, the content of which is hereby incorporated by reference.

Said set preferably additionally comprises at least one tool with a mating contour which is complementary to the contour of the recess. By way of the tool, it is possible, for example after the breaking-off of the insertion post, for the screw to be tightened yet further, and/or, after the healing of a bone fracture, for said screw to be released again and removed.

The invention furthermore relates to a method for producing a screw having an insertion post. Said method comprises the step of providing a screw body having a screw head, shank and screw tip and having an insertion post which is integrally connected to the screw. The screw body has a recess with a contour for a tool. The insertion post is connected by way of a predetermined breaking point to a post tip, wherein the predetermined breaking point is arranged within the recess.

The invention also relates to a method for producing a screw having an insertion post, which method comprises the following steps:
- providing a screw body having a screw head, a shank and a screw tip, wherein the screw body has a recess with a contour and an adjoining opening for receiving the insertion post,
- providing an insertion post which is connected by way of a predetermined breaking point to a post tip,
- joining the insertion post and the screw body together by way of the post tip and the opening for receiving the insertion post.

In a preferred method, the insertion post is screwed into the screw body. The insertion post is preferably additionally pressed together with the screw body from the outside.

Alternatively, the insertion post may also be only pressed into the screw body.

Alternatively, the insertion post may be adhesively bonded, crimped, shrink-fitted, welded or connected by way of some other suitable method into the screw body.

The insertion post is preferably connected to the screw body by way of a combination of the described methods.

In an alternative preferred method, the screw and insertion post are produced integrally, that is to say without a joining process.

Further advantageous refinements of the invention will emerge from the following description of the exemplary embodiments in conjunction with the schematic figures. In the figures, in each case schematically:

FIGS. 1a/b: show a longitudinal section through a first embodiment of a screw according to the invention.

Figure 2:
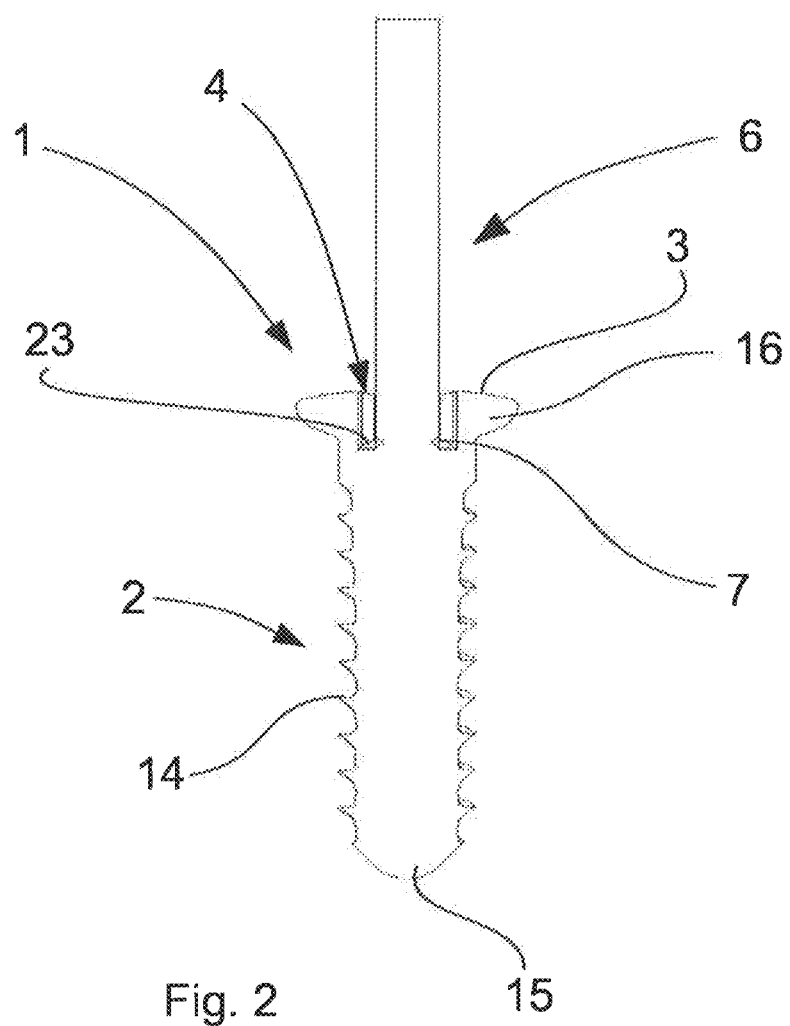

FIG. 2: shows a longitudinal section through an alternative embodiment of a screw according to the invention.

Figure 3:
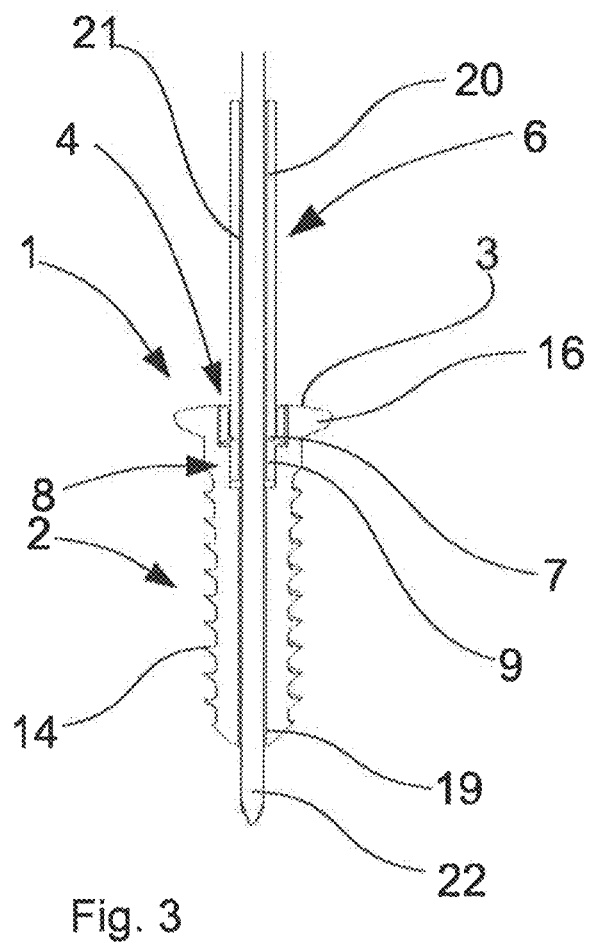

FIG. 3: shows a longitudinal section through a further embodiment of a screw according to the invention.

Figure 4:
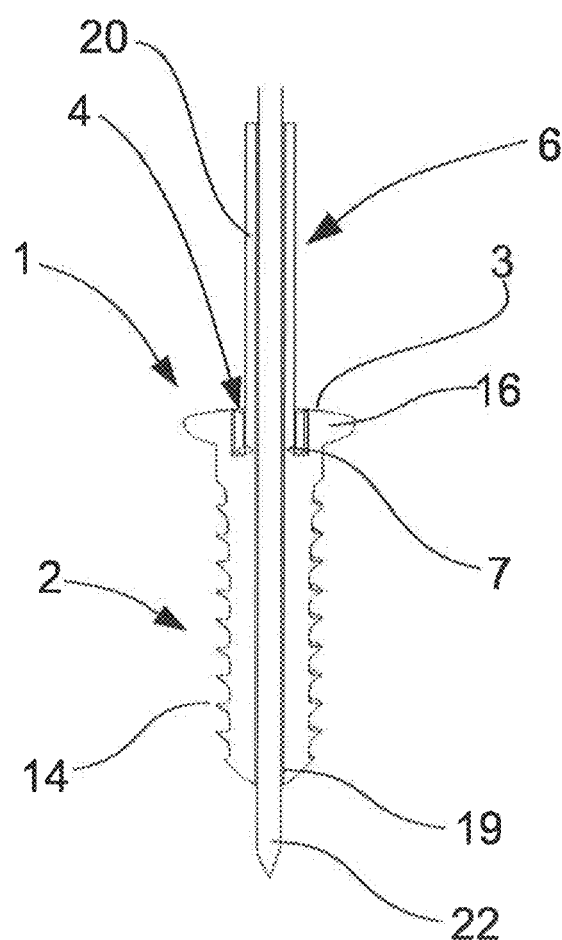

FIG. 4: shows a longitudinal section through a further embodiment of a screw according to the invention.

Figure 5A:
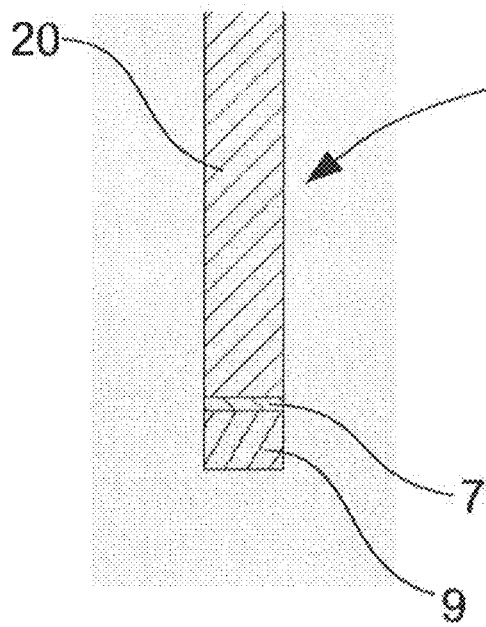

FIGS. 5a/b/c: show detail views of insertion posts according to the invention with different predetermined breaking points.

Figure 6:
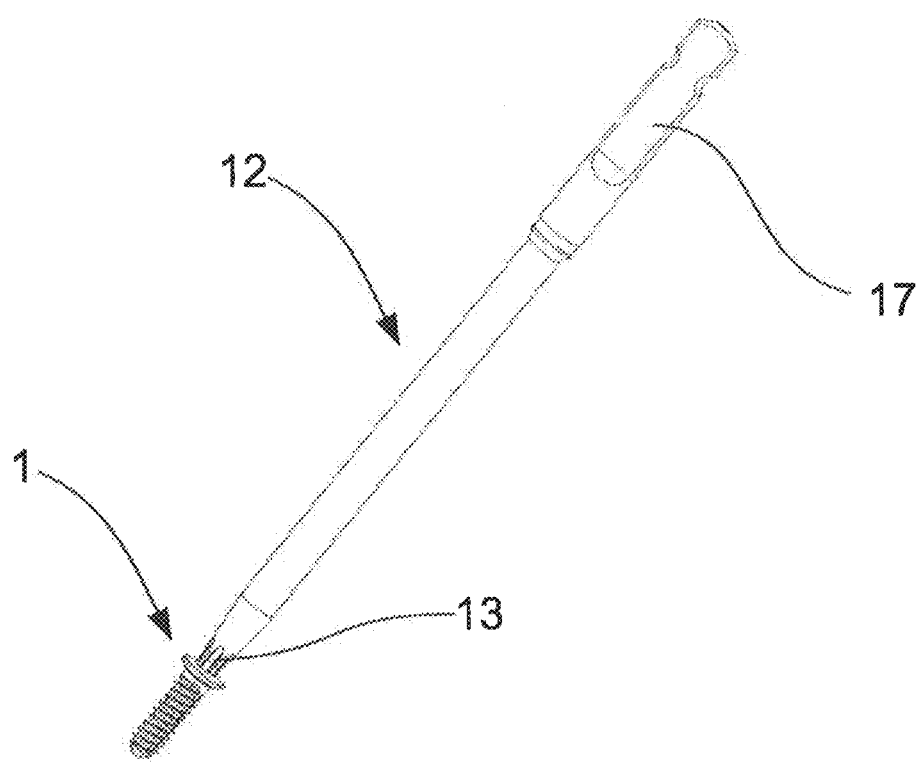

FIG. 6: shows a screw according to the invention after the twisting-off/breaking-off of the insertion post, with a tool.

Figure 7:
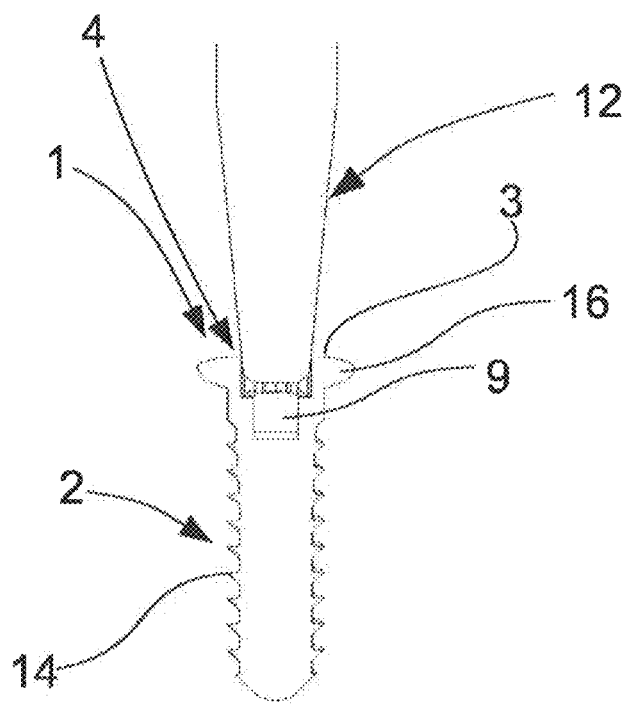

FIG. 7: shows a longitudinal section through a first embodiment of a screw according to the invention after the twisting-off/breaking-off of the insertion post, with a tool.

Figure 8:
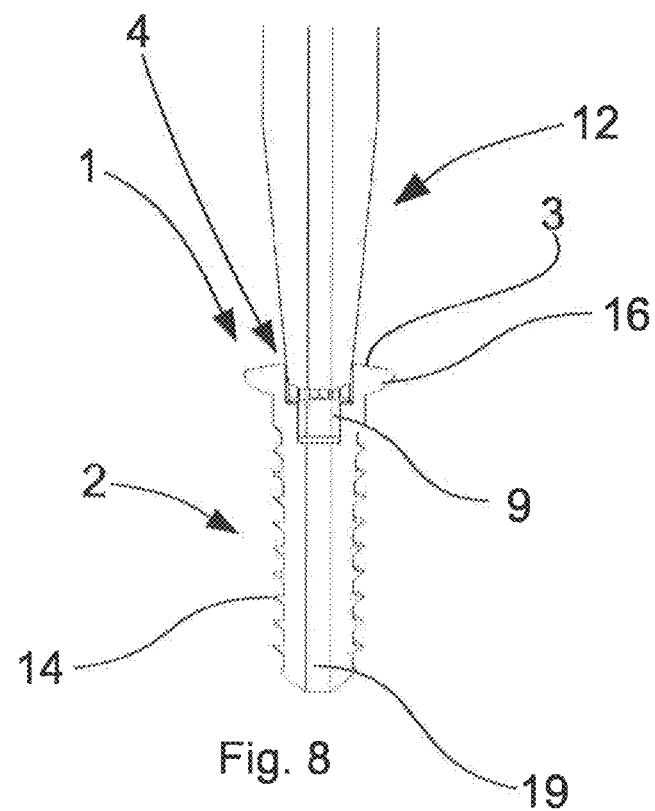

FIG. 8: shows a longitudinal section through an alternative embodiment of a screw according to the invention after the twisting-off/breaking-off of the insertion post, with a tool.

Figure 9:
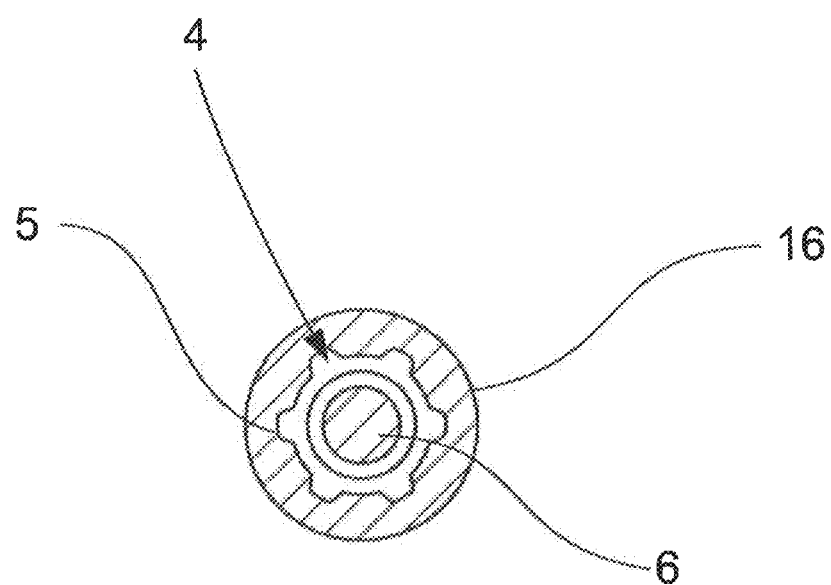

FIG. 9: shows a cross section through a screw head of a screw according to the invention with insertion post.

Figure 1B:
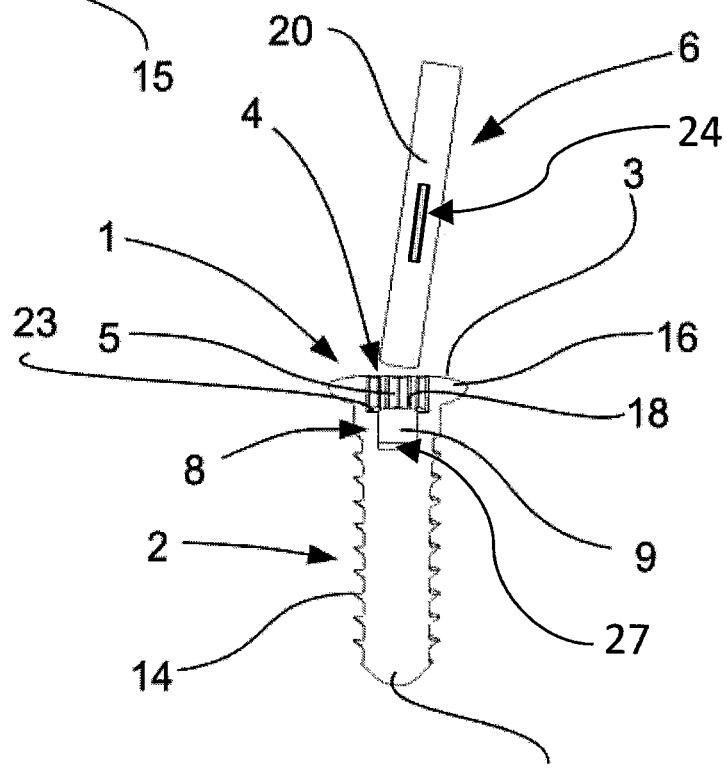

FIGS. 1a and 1b show a longitudinal section through a first embodiment of a screw 1 according to the invention. The screw 1 has a shank 2 which is equipped with a thread 14. The screw 1 furthermore has a tip 15 and a screw head 16 situated opposite the tip 15. The screw head 16 has a head side 3. On the head side 3 there is formed a recess 4. An opening 8, which can be a blind hole 27 for receiving a post tip 9 of an insertion post 6 is provided so as to adjoin the recess 4. The opening 8 for receiving the post tip 9 has an internal thread (not shown). The tip 9 has an external thread (not shown) which can be screwed into the internal thread of the opening 8, which is diagrammatically indicated by arrow 25.

In FIG. 1a, the post tip 9 is connected by way of a predetermined breaking point 7 to a post shank 20 of the insertion post 6. The post shank 20 is only partially illustrated in FIGS. 1a and 1b. The insertion post may comprise product-specific labeling 24, such as a batch number, a barcode or a logo. The predetermined breaking point 7 is in this case in the form of a constriction between the tip 9 and the post shank 20. The insertion post 6 is thus connected indirectly to the screw 1 by way of the predetermined breaking point 7. The indirect connection of post tip and screw may be realized by way of a conical or cylindrical thread, by way of pressing (diagrammatically indicated by arrow 26), adhesive bonding, shrink-fitting, crimping or other connection methods, or by way of a combination of several of said connection methods. In the case of a connection that is realized for example only by way of pressing, adhesive bonding, shrink-fitting or crimping, the threads may also be omitted.

As the screw 1 is screwed in, the torque increases. The predetermined breaking point 7 is designed so as to break before the tightening torque is reached. In FIG. 1b, the post shank 20 of the insertion post 6 has broken off from the post tip 9 at the predetermined breaking point 7. The post tip 3 thus has a break point 18. The break point 18 is situated approximately at the level of the base surface 23 of the recess 4. In this way, the break point 18 does not come into contact with surrounding tissue, whereby irritation of said tissue is prevented.

The recess 4 has a contour 5. The contour is in the form of a hexalobular socket. After removal of the post shank 20 of the insertion post 6, the contour 5 is exposed. A tool 12 (see e.g. FIG. 6) with a matching mating contour 13 (see e.g. FIG. 6) can be placed in operative connection with the contour 5. By way of the tool 12, the screw 1 can be screwed into an end position. The screw 1 can also be unscrewed by way of the tool 12 when the screw 1 is no longer required.

FIG. 2 shows an alternative embodiment according to the invention of the screw 1. The insertion post 6 and the screw 1 are in this case of integral form. The two parts are manufactured from one piece of material. The predetermined breaking point 7 in this case directly forms the connecting point between the insertion post 6 and the screw 1. After a breaking-off of the insertion post 6 at the predetermined breaking point 7, a break point 8 will again be situated approximately at the level of the base surface 23 of the recess 4 (not shown). The recess again has a contour 5 by way of which the screw 1 can be screwed in further or unscrewed with the aid of the tool 12 (not shown) after the breaking-off of the predetermined breaking point 7.

FIG. 3 shows a farther embodiment of a screw 1 according to the invention. The screw 1 and the insertion post are, as in the embodiment of FIGS. 1a and 1b, connected indirectly by way of the predetermined breaking point 7. In this embodiment, the screw 1 is cannulated. The cannulation 19 extends in this case over the entire shank 2 of the screw 1. The insertion post also has a cannulation 21. The cannulations 19, 21 are fluidically connected when the insertion post 6 is in a screwed-in state. In this way, a continuous cannulation is realized.

Within the cannulations 19, 21 there is situated a wire 22, a so-called Kirschner wire or K-wire. Such wires 22 are used in various orthopedic and other operations. The wire 22 is inserted, into the bone. By way of the cannulation 19, 21, the screw 1 can be introduced over the wire 22 into the bone. Here, the wire 22 serves as a guide.

FIG. 4 shows a further embodiment of a screw 1 according to the invention. As in FIG. 3, a cannulation 19 is provided in the screw 1. The insertion post 6 and the screw 1 are, as in FIG. 2, of integral form. The cannulation 15 is formed all the way through the screw 1 and the insertion post 6. A wire 22 is again shown within the cannulation 19. The screw 1 has again been introduced by way of the cannulation 19 and the wire 22.

FIGS. 5a, b, c show detailed views of insertion posts 6. The insertion posts 6 nave post tips 9 and post shanks 20, which are connected to one another by way of predetermined breaking points 7.

In the embodiment shown in FIG. 5a, the predetermined breaking point 7 has been realized as a material variation. The predetermined breaking point 7 is thus formed with a material which is weaker in terms of failure than the post tip 9 and the post shank 20. The post tip 9 and the post shank 20 are for example manufactured from titanium, and the predetermined breaking point is manufactured for example from a biocompatible plastic which adhesively bonds the two parts. In this way, the predetermined breaking point 7 will fail at a certain torque.

Figure 5B:
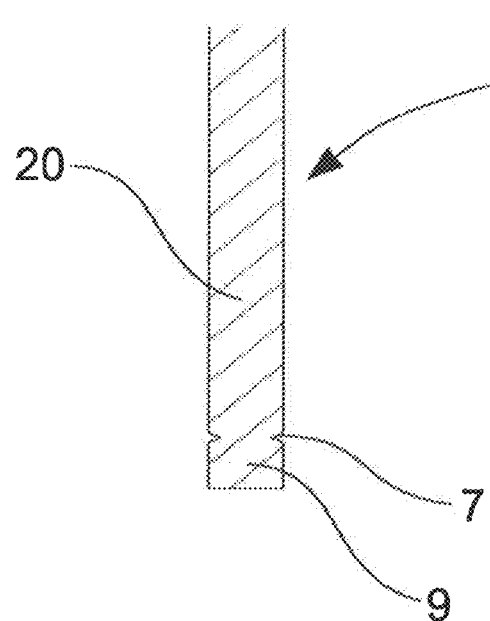

In the embodiment shown in FIG. 5b, the predetermined breaking point 7 is in the form of a construction. The constriction has been formed by way of material removal at that location. The post tip 9 and the post shank 20 are of integral form.

Figure 5C:
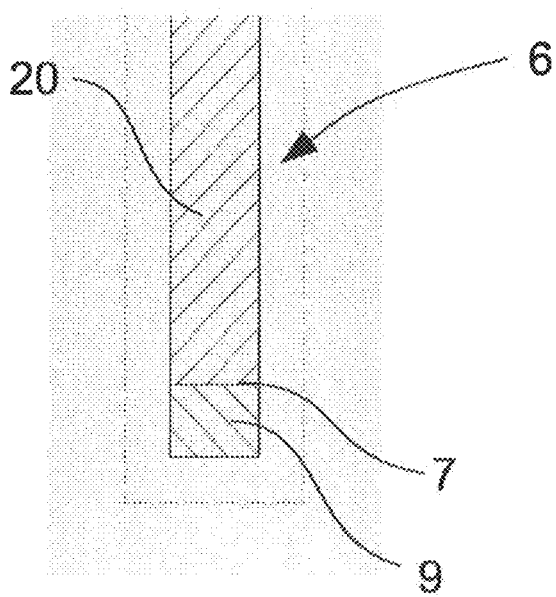

In the embodiment shown in FIG. 5c, the predetermined breaking point has been formed by way of a connection with a reduced resistance to bending and torsion moments. Such connections may for example be welded connections. Alternative connections are pressed connections, shrink-fitted connections, crimped connections, adhesively bonded connections and other suitable connections, and also combinations of the connections.

FIG. 6 shows a screw 1 according to the invention after removal, of the post shank 20 of the insertion post 6 (not shown). A tool 12 has been inserted into the recess 4 (not visible in FIG. 6). Here, a mating contour 13 of the tool 12 is in operative connection with the contour 5 (not visible in FIG. 6) of the recess 4 (not visible in FIG. 6). The screw 1 can be screwed in yet further by way of the tool 12. When the screw is no longer required or must be explanted, the screw can be released by way of the tool 12.

The contour 5 (not visible) of the recess is for example in the form of a hexalobular socket. This common contour ensures that the screw 1 can be screwed in further and unscrewed by way of a standardized tool 12.

The tool 12 has, at an end situated opposite the mating contour 13, a connecting section 17, The connecting section 17 serves for the connection of the tool 12 to a screwing-in aid (not shown) such as for example a drilling machine or a screwdriver handle.

FIG. 7 shows a longitudinal section through the screw 1 of FIGS. 1a, b, after the post shank 20 of the insertion post 6 (not shown) has been removed and the tool 12 has been inserted, by way of the mating contour 13, into the recess 4.

FIG. 8 shows a longitudinal section through the screw 1 of FIG. 3, after the post shank 20 of the insertion post 6 (not shown) has been removed and the tool 12 has been inserted, by way of the mating contour 13, into the recess 4.

FIG. 9 shows a cross section through a screw head 16 at the level of the predetermined breaking point 7 of a screw 1 according to the invention with insertion post 6. The recess 1 of the screw head 16 has a contour 5 in the form of a hexalobular socket. After removal of the insertion post 6, the screw 1 can, by way of the contour 5, be screwed in yet further or unscrewed using the suitable tool 12 (not shown in FIG. 9).

The invention claimed is:

1. A screw, in particular bone screw, having a head, a shank and a tip, and the screw, at a head side, having a recess with a screw contour,
   wherein the screw is equipped, in the recess, with an insertion post which is connected to the screw by way of a predetermined breaking point,
   after breaking of the predetermined breaking point, a mating contour of a tool can be placed in operative connection with the screw contour of the recess,
   the predetermined breaking point is arranged within the recess such that, after removal of the insertion post, a transmission of torque between the tool and the screw is possible by way of the screw contour and the mating contour,
   wherein
   the screw contour of the recess is in the form of one of a hexagon socket, a hexalobular socket, a square socket, or a Phillips socket,
   and the insertion post is equipped, integrally by way of the predetermined breaking point, with a post tip, wherein the post tip is separated from a rest of the insertion post, as a result of breaking of the predetermined breaking point, such that the post tip remains in the screw after breaking of the insertion post at the pre-determined breaking point, and the post tip has a tip contour for transmission of torque via a mating contour in the recess of the screw,
   such that transmission of torque, from the insertion post to the screw, is possible by way of the post tip, and
   the screw can be screwed in by way of the insertion post, and
   the breaking point is situated approximately at a level of a base surface of the recess.

2. The screw according to claim 1, wherein the predetermined breaking point is arranged so as to be set back relative to an end surface of the screw.

3. The screw according to claim 1, wherein the recess has an opening adjoining the screw contour and, prior to separation of the post tip from the rest of the insertion post, a portion of the insertion post, located within the recess, is spaced from the screw contour so as to be out of contact therewith.

4. The screw according to claim 1, wherein the screw and the insertion post have a cannulation.

5. The screw according to claim 1, wherein the predetermined breaking point is formed as a material weakening in a form of a constriction.

6. The screw according to claim 1, wherein the insertion post is formed separately from the post tip and is connectable or connected to the post tip by way of the predetermined breaking point, and the post tip has the tip contour for transmission of torque via the mating contour in the recess.

7. The screw according to claim 1, wherein the predetermined breaking point is designed so as to break in a presence of torque lower than the breakaway torque of the bone.

8. The screw according to claim 1, wherein the insertion post and the screw are formed integrally with one another.

9. The screw according to claim 1, wherein the insertion post is screwed into a blind hole.

10. The screw according to claim 1, wherein the insertion post is pressed into a blind hole of the recess.

11. The screw according to claim 1, wherein the screw and the insertion post comprise a biocompatible material from a list consisting of titanium, titanium alloys, steel, plastic, absorbable metal or absorbable plastic.

12. The screw according to claim 1, wherein the insertion post comprises a product-specific labelling which can be at least one of read off and preserved after breaking of the predetermined breaking point.

13. The screw according to claim 1, wherein operative connection of the mating contour of the tool with the screw contour of the screw is only possible after the insertion post is broken away at the predetermined breaking point and removed from the screw.

14. A set having at least one tool having a mating contour with respect to the screw contour of the recess of the screw and having at least one screw according to claim 1.

15. The set according to claim 14, which additionally comprises a bone plate.

16. A method of producing a screw having an insertion post, the method comprising:
   providing a screw body which has a screw head, a shank and a screw tip, wherein the screw body has a recess with a screw contour for a tool, and providing an insertion post which is integrally connected to the screw and which is connected thereto by way of a predetermined breaking point to a post tip,
   wherein the predetermined breaking point is arranged within the recess, and the post tip has a tip contour for transmission of torque via a mating contour in the recess of the screw and the post tip is completely separated from a rest of the insertion post as a result of breaking of the insertion post from a remainder of the screw at the predetermined breaking point.

17. The method for producing a screw according to claim 16, wherein operative connection of a mating contour of the tool with the screw contour of the screw is only possible after the insertion post is broken away at the predetermined breaking point and removed from the screw.

18. A method for producing a screw having an insertion post, the method comprising:
   providing a screw body having a head, a shank and a tip, wherein the screw body has a recess with a screw contour and an adjoining opening,
   providing a post which is connected by way of a predetermined breaking point to a post tip, wherein the post tip can be separated from a rest of the insertion post as a result of breaking of the predetermined breaking point, and the post tip has a tip contour for transmission of torque via a mating contour in the recess of the screw, and
   joining the post and the screw body together by way of the post tip and the opening.

19. The method according to claim 18, further comprising screwing the post into the screw body.

20. The method according to claim 18, further comprising pressing the post into the screw body.

21. The method for producing a screw according to claim 18, wherein operative connection of a mating contour of a tool with the screw contour of the screw is only possible after the insertion post is broken away at the predetermined breaking point and removed from the screw.

* * * * *